United States Patent [19]

Quaranta et al.

[11] Patent Number: 5,510,263
[45] Date of Patent: Apr. 23, 1996

[54] GROWTH OF PANCREATIC ISLET-LIKE CELL CLUSTERS

[75] Inventors: Vito Quaranta, La Jolla, Calif.; Jonathan C. R. Jones, Chicago, Ill.

[73] Assignee: Desmos, Inc., San Diego, Calif.

[21] Appl. No.: 152,460

[22] Filed: Nov. 12, 1993

Related U.S. Application Data

[63] Continuation-in-part of Ser. No. 42,727, Apr. 5, 1993, abandoned.

[51] Int. Cl.⁶ .............................. C12N 5/00; C12N 5/06; C12N 5/08; A61K 35/22
[52] U.S. Cl. .................. 435/240.243; 435/240.2; 435/240.21; 435/240.23; 424/558
[58] Field of Search ................ 435/240.2, 240.21, 435/240.23, 240.243; 424/558

[56] References Cited

U.S. PATENT DOCUMENTS 5,007,925   3/1991   Tsilibary et al. .................. 623/1

FOREIGN PATENT DOCUMENTS 9217498   10/1992   WIPO.
9405316    3/1994   WIPO.

OTHER PUBLICATIONS

Jones et al., J. Cell Biochem., Supp. 16F: 142, p. 142 (abstract #X 008) (Apr. 1992).
Langhofer et al. Mol. Bio. Cell, vol. 3, Supp 1, p. 95a (abstract #550) (1992).
Hormia et al, Int. Assoc. for Dental Research (Feb. 1993). Mol. Bio. Cell, vol. 3, p. 70a (abstract #404) (1992).
Riddelle et al., J. Cell Biol, vol. 109, p. 201(a) (1989).
Riddelle et al., J. Cell Biol, vol. 113, p. 41(a) (1991).
Hopkinson et al, J. Cell Biol. vol. 111, p. 408a (1990).
Kurpakus et al, J. Cell Biol. vol. 111, p. 402a (1990).
Jones et al. (1992) Integrins: Their role in the Assembly of the Hemidesmosome (HD) and in Signal Transduction. J. Cell Biochem., vol. 142, Suppl 16F, p. 142 Abstr. X 007.
Langhofer et al. (1992) Matrix Signals Transduced by the alpha–686 Integrin Complex. Mol. Biol. Cell, vol. 3 p. 95a, Abstr. 550.
Riddelle et al. (1991) Formation of Hemidesmosomes in Vitro by a Transformed Rat Bladder Cell Line. J. Cell Biol., vol. 112, No. 1, pp. 159–168.
Beattie, et al. Functional Impact of Attachment and Purification in the Short Term Culture of Human Pancreatic Islets, *Journal of Clinical Endocrinology and Metabolism* 73:1 pp. 93–98, (1991).
Brewin, et al. Limited Survival of Human Preislet Cells Transplanted into Diabetic Renal Transplant Recipients After 15 Months *Transplantation Proceedings* 22:2 pp. 756–757, (1990).
Chapman, et al. Abnormal Expression of Hemidesmosome--Like Structures by Junctional Epidermolysis Bullosa Keratinocytes in Vitro *British Journal of Dermatology* 122:137, (1990).

Giudice, et al. Identification of Two Collagen Domains Within The Bullous Pemphigold Autoantigen, BP–180, *J. Clin. Invest.* 87:734, (1991).
Hayek, et al., Intrapancreatic Islet Transplantation in Experimental Diabetes in the Rat *Metabolism* 41:12 pp. 1367–1369, (1992).
Hieda, et al., Identification of a New Hemidesmosomal Protein, HD1: A Major, High Molecular Mass Component of Isolated Hemidesmosomes, *The Journal of Cell Biology* 116:1497, (1992).
Hopkinson, et al. Cytoplasmic Domain of the 180kD Bullous Pemphigoid Antigen, A Hemidesmosomal Component; Molecular and Cell Biologic Characterization, *The Journal of Investigative Dermatology* 99:264, (1992).
Izumi, et al. In Vitro Induction of Ornithine Decarboxylase in Urinary Bladder Carcinoma Cells, *Cancer Research* 115:1736, (1991).
Kover, et al. Development of a Method of Isolation of Islets from Human Fetal Pancreas *Diabetes* 38: pp. 917–924, (1989).
Kurpakus, et al., Surface Relocation of Alpha₆Beta₄ Integrins and Assembly of Hemidesmosomes in an In Vitro Model of Wound Healing, *The Journal of Cell Biology* 115:1737, (1991).
Langhofer, et al., The Matrix Secreted by 804G Cells Contains Laminin–Related Components that Participate in Hemidesmosome Assembly in Vitro *Journal of Cell Science* 105: pp. 753–764, (1993).
Leach, et al., Insulin Release from Human Foetal Pancreas in Tissue Culture *J. Endocr.* 59: pp. 65–79, (1973).
Lopez, et al., Factors Influencing Islet Transplantation *Transplantation* 49:1 pp. 224–225, (1990).
Maugh, et al. Implants: A New Shot at Controlling Diabetes *Los Angeles Times* pp. E5–E6 (1993).
Noonan, et al. Transplantation of Monolayer Cultured Human Pancreatic Cells in Diabetic Nude Mice (Abstract) *Diabetes* 36(supl. 1): p. 40A, (1987).
Otonkoski, et al. Morphology, Yield and Functional Integrity of Islet–Like Cell Clusters in Tissue Culture of Human Fetal Pancreata Obtained After Different Means of Abortion *Acta Endocrinologica* (Copenh) 188: pp. 68–76, (1988).
Sandler, et al. Tissue Culture of Human Fetal Pancreas: Development and Function of B–Cells in Vitro and Transplantation of Explants to Nude Mice *Diabetes* 34: pp. 1113–1119, (1985).
Simpson, et al., Characterization of Endocrine–Rich Monolayers of Human Fetal Pancreas That Display Reduced Immunogenicity *Diabetes* 40: pp. 800–808, (1991).
Simpson, et al., Pig Fetal Pancreatic Monolayers *Transplantation* 49:6 pp. 1133–1137, (1990).

(List continued on next page.)

*Primary Examiner*—Michael G. Wityshyn
*Assistant Examiner*—Susan M. Dadio
*Attorney, Agent, or Firm*—Knobbe, Martens, Olson & Bear

[57] ABSTRACT

A method for growing endocrine precursor cells in vitro, such as pancreatic islet precursors, by culturing such cells in the presence or absence of cell matrix proteins capable of promoting hemidesmosome formation, such as those produced by the rat bladder carcinoma cell line 804G.

7 Claims, No Drawings

OTHER PUBLICATIONS

Sonnenberg, et al., Integrin α6/β4 Complex is Located in Hemidesmosomes, Suggesting a Major Role in Epidermal Cell–Basement Membrane Adhesion *The Journal of Cell Biology* 113:907, (1991).

Staehelin, et al., Structure and Function of Intercellular Junctions, *Department of Molecular, Cellular and Development Biology*, University of Colorado, Boulder, Colorado pp. 191–283.

Stepp, et al., $\alpha_6\beta_4$ Integrin Heterodimer is a Component of Hemidesmosomes *Proc. Natl. Acad. Sci. USA* 87:8970, (1990).

Voss, et al. Transplantation of Proliferated Human Pre–Islet Cells into Diabetic Patients with Renal Transplants *Transplantation Proceedings* 21:1 pp. 2751–2756, (1989).

Weitzman, et al. The Function and Distinctive Regulation of the Integrin VLA–3 In Cell Adhesion, Spreading, and Homotypic Cell Aggregation *The Journal of Biological Chemistry* 268:12 pp. 8651–8657, (1993).

GROWTH OF PANCREATIC ISLET-LIKE CELL CLUSTERS

GOVERNMENT SUPPORT

This research was supported by National Institutes of Health Grant GM 38470. The government may have certain rights in the invention.

This application is a continuation-in-part of U.S. Ser. No. 08/042,727 filed Apr. 5, 1993, now abandoned which is hereby expressly incorporated by reference.

BACKGROUND

When organs of the body are formed, they develop as neatly organized arrays of cells. Often, cell groups of one kind are separated from cells of another kind by flat strips of connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut.

Basement membranes have been implicated in the growth, attachment, migration, repair, and differentiation of their overlying cell populations. Three layers have been defined in basement membranes: a) the *Lamina lucida*, an electronmicroscopically clear region that resides in close approximation to the overlying cells; b) the lamina densa, an electron dense region of 20–300 nm in width; and c) the sublamina densa that contains anchoring fibrils, microfibrillar bundles and collagen fibers.

Many different types of compounds have now been localized to the basement membrane. Some of these compounds are laminin, collagen IV and heparin sulfate proteoglycans (Verrando et al. Exp. *Cell Res.* (1987); 170: 116–128). In addition, specific basement membranes include other biologically active components, such as nidogen and entactin.

One major cell adhesion receptor that epidermal cells use to attach to the basement membrane is called $\alpha 6 \beta 4$. This transmembrane receptor is formed by a combination of two protein moieties $\alpha 6$ and $\beta 4$. The $\alpha 6$ and $\beta 4$ proteins are derived from different genes that have been found to be part of the integrin family.

Integrins are versatile family cell adhesion receptors. So far, approximately twenty members have been discovered in the integrin family. These molecules are involved in many types of cell adhesion phenomena in the body. Integrins are signalling molecules that can translate environmental cues into cellular instructions. Further, integrins can also transmit signals in the reverse direction, from the cell interior to the exterior. This has been illustrated in non-adherent cells, such as lymphocytes.

Stimulation of the T-cell antigen receptor, or of the CD3 complex, augments the affinity of certain integrins for their respective ligands. Unfortunately, in adherent cells, changes in the affinities of integrins have been more difficult to demonstrate. However, affinity modulation of one integrin in differentiating epidermal keratinocytes has been described by Adams et al. (*Cell* (1990); 63: 425–435). For this reason, modifications of cell status initiated by activation or differentiation of other receptors may influence integrin affinity, and ultimately, the adhesive behavior of cells. Further, as a consequence of adhering to a surface, an integrin may actively contribute to modifying cell shape or migration.

Many epithelial cells interact with the underlying extracellular matrix via a junction called the hemidesmosome (Staehelin, 1974). Over the last few years there has been considerable progress in the biochemical characterization of this junction (Schwartz, et al., 1990). The hemidesmosome, with its associated structures such as intermediate filaments and anchoring fibrils, forms an adhesion complex. Disruptions of the epithelial-connective tissue interaction are often accompanied by disruption of the hemidesmosome complex. For example, in certain blistering skin diseases such as junctional epidermolysis bullosa where epithelial cell-connective tissue interaction is abnormal, it has been proposed that there is a biochemical modification in or loss of a basement membrane zone-associated component of the hemidesmosome.

Two high molecular weight intracellular components of the hemidesmosome have been identified and characterized with the aid of antisera from patients suffering from bullous pemphigoid. This autoimmune disease results in a disruption of the interactions between epithelial cells and connective tissue simultaneously with loss of hemidesmosome integrity (Stanley, (1993) *Adv. Immunol.*, 63: 291–325). Accordingly, it was discovered that bullous pemphigoid patients were producing antibodies against hemidesmosome components. Two hemidesmosome related bullous pemphigoid (BP) antigens have been previously described (Klatte, et al., 1989).

One BP antigen is a 230 kD polypeptide that may act as an anchor for cytoskeleton elements in the hemidesmosomal plaque (Jones and Green, 1991). A second BP antigen is a type II membrane protein that possesses a collagen-like extracellular domain (Giudice, et al., 1991; Hopkinson, et al., 1992). In addition, it has been demonstrated that the interaction of the hemidesmosome with the underlying connective tissue involves the $\alpha_6\beta_4$ integrin heterodimer (Stepp, et al., 1990; Jones, et al., 1991; Sonnenberg, et al., 1991; Kurpakus, et al., 1991). The $\alpha_6\beta_4$ heterodimer has been localized to hemidesmosomes along the basal surfaces of the rat bladder carcinoma cell line 804G (Jones et al. *Cell Regulation* (1991); 2: 427–438). These results suggested that integrins (e.g. $\alpha_6\beta_4$) may play an important role in the assembly and adhesive functions of hemidesmosomes.

Various prior art efforts have focused on purifying adhesion-facilitating proteins found in basement membrane. For example, Burgeson, et al., Patent Cooperation Treaty Application No. WO92/17498, disclose a protein which they call kalinin. Kalinin is said to facilitate cell adhesion to substrates; however, this material is apparently inactive with respect to hemidesmosome formation. See also, Marinkovich, et al., *J. Cell Biol.* (1992); 119:695–703 (klaminin); laminin Rouselie, et al., *J. Cell. Biol.* (1991); 114:567–576 (kalinin); and Marinkovich, et al., *J. Biol. Chem.* (1992); 267:17900–17906 (kalinin).

Similarly, a basement glycoprotein of about 600 kD made up of polypeptides in the range of 93.5 kD to 150 kD has been identified, and is known as GB3 or nicein. See, e.g., Verrando, et al., *Biochim. Biophys. Acta* (1988); 942:45–56; and Hsi, et al., *Placenta* (1987); 8:209–217. None of these materials have been effective in generating formation of hemidesmosomes, either in vitro or in vivo.

When cultured on tissue culture plastic in vitro, most epithelial cells do not assemble bona fide hemidesmosomes despite the fact that they appear to express all of the hemidesmosomal plaque and transmembrane components mentioned above. Indeed, it is only recently that cell lines such as 804G were discovered to have the ability to readily assemble hemidesmosomes in vitro under regular culture conditions (Riddelle, et al., 1991; Hieda, et al., 1992). Such cells are at last allowing detailed cell and biochemical analysis of the dynamics of hemidesmosome assembly.

For instance, it has been reported that substratum-associated staining by anti-hemidesmosome antibodies is greatly diminished in 804G cell cultures that enter in vitro wound sites (Riddelle et al., *J. Cell Sci.* (1992); 103: 475–490). However, as closure of the wound became complete, anti-hemidesmosome staining along the substratum-attached surface was evident in the cells.

There are, however, many epithelial cells that do not attach to tissue culture dishes in a normal fashion, even after treatment with various growth factors. These cells do not produce normal hemidesmosomes or grow to resemble their in vivo phenotype. It would provide a tremendous advantage to have a system that was capable of maintaining epithelial cell growth in vitro wherein the cells maintained their normal phenotype.

Nearly two million Americans are afflicted with Type I (insulin-dependent) diabetes, in which the pancreas has lost its ability to secrete insulin due to an autoimmune disorder in which the insulin-secreting beta cells, found within the islet cells of the pancreas, are destroyed. Although insulin injections can compensate for beta cell destruction, blood sugar levels can still fluctuate dramatically. The impaired ability to take up glucose from the blood results in side reactions in which toxic products accumulate, leading to complications including blindness, kidney disease, nerve damage, and, ultimately, coma and death.

Researchers have tried smaller, more frequent doses of insulin and mechanical pumps which mimic the action of the pancreas, but the results have been far from ideal. Another option, pancreatic transplant, requires major surgery and is accompanied by many complications. In addition, the limited number of donor pancreases leaves a significant number of diabetics without hope for transplantation.

The most promising option thus far is islet cell transplantation using tissue derived from either cadavers or human fetuses. This procedure has had moderate success. Among the transplants from cadavers performed worldwide, the transplanted tissue survived for a full year in about 20% of recipients. Ten of these recipients are now insulin-independent, while others have a greatly reduced need for insulin. The main problems associated with islet cell transplantation include rejection by the immune system and the autoimmune disorder which caused the disease in the first place which, if left unchecked, will also destroy the transplanted islet cells.

Islet-like cell clusters (ICCs) are composed of a heterogeneous cell population. In addition to epithelial cells which differentiate to form the endocrine, exocrine and ductal tissues, the clusters contain many stromal cells, primarily fibroblasts and endothelial cells. The presence of large numbers of stromal cells complicates the issue due to difficulties in quantitating important measures of differentiation such as insulin content per cell (Beattie et al., (1991) *J. Clin. Endocrinol. Metab.*, 73: 93–98). Also, the effects of growth and differentiation factors on endocrine precursor cells from ICCs are complicated by the presence of stromal cells.

Fetal pancreatic tissue has certain advantages over adult pancreas as a source of islet cells including its greater content of islets in proportion to its mass, its less mature endocrine cells and its greater capacity for proliferation (Voss et al., (1989) *Transplantation Proc.*, 21: 2751–2756). It is hoped that fetal islet cell transplants will dramatically reduce or eliminate diabetics' insulin dependence in a majority of patients in controlling blood sugar levels, thus minimizing the most severe diabetic complications.

Earlier attempts at culturing pancreatic islet cells were complicated by fibroblast contamination (Leach et al., (1973) *J. Endocrinol.*, 59: 65–79). Although partially digested fetal pancreas has been used to produce ICCs, the clinical use of these clusters is limited because only 100–200 can be obtained per pancreas (Sandler et al., (1985) *Diabetes*, 34: 1113–1119; Otonkoski et al., (1988) *Acta. Endocrinol.*, 118: 68–76). Kover and Moore (*Diabetes*, 38: 917–924 (1989)) obtained 200–300 islets from a 17 week fetal pancreas, still not enough to be clinically useful. Finally, Simpson et al. (*Diabetes*, 40: 800–808 (1991)) were able to generate insulin-secreting, fibroblast-free monolayers of human fetal pancreas plated on bovine corneal matrix, although adequate numbers of cells for clinical transplantation were still not obtained. Although only a small number of cells within the clusters stain positively for the different pancreatic hormones, they differentiate efficiently into mature endocrine cells following transplantation into nude mice (Sandler et al., (1985) *Diabetes*, 34: 1113–1119).

Expansion of the pool of available islet cells for transplantation is highly desirable because the current technology will not produce enough cells for routine transplantation.

SUMMARY OF THE INVENTION

One embodiment of the present invention is a method for enhancing the growth of endocrine precursor cells by culturing the cells in the presence of 804G matrix. Preferably, the endocrine precursor cells are pancreatic islet cell precursors. This embodiment further provides, prior to the culturing step, enzymatically digesting fetal pancreas and incubating the digested tissue in medium until islet-like cell aggregates are formed. Preferably, the pancreas is human and the 804G matrix proteins are attached to a substrate. Another aspect of the invention provides that the 804G matrix is derived from 804G rat bladder carcinoma cells.

Another embodiment of the invention is a method for the generation of hormone-producing cells by producing expanded endocrine precursor cells and transplanting these cells into a mammal. Preferably, these cells are pancreatic islet cells, the hormone is insulin and the transplantation site is either the kidney, lung or liver.

The present invention also provides expanded endocrine precursor cells which are preferably fetal pancreatic islet precursor cells.

Detailed Description of the Invention

The present invention includes the discovery that certain cell lines produce an extracellular matrix that is capable of stimulating cellular adhesion and hemidesmosome assembly in other cells subsequently grown on the matrix. One such cell line is the bladder carcinoma cell line 804G. This cell line is described by Izumi, et al., *Cancer Res.* (1981); 41:405–409, and is maintained in permanent collection in the laboratory of Jonathan C. R. Jones. This cell line is also available from Ryoichi Oyasu, Department of Pathology, Northwestern University Medical School, Chicago, Ill. The 804G cell line has also been deposited as a budapest Treaty Deposit with the American Type Culture Collection, Rockville, Md., on Feb. 24, 1994, under Accession Number CRL 11555. The NBT II cell line referred to herein has been deposited as a Budapest Treaty Deposit with the American Type culture Collection, Rockville, Md., under Accession Number CRL 11556.

Ultrastructural data have been developed demonstrating that the 804G matrix is capable of inducing a number of cells to develop mature hemidesmosomes and attach to their growth substrate. Further, it has been discovered that the 804G matrix contains novel laminin-like molecules that participate in hemidesmosome assembly (unlike laminins and related molecules that have been purified in the prior art). Three of these molecules have been cloned from a rat 804G cDNA library and encode proteins of 150, 140 and 135 kDa. Analysis of two cDNAs encoding the 140 kDa protein revealed sequence similarity with human laminin B2t (Kallunki et al., (1992) *J. Cell Biol.,* 119: 679–695). A novel matrix can now be prepared, produced by such cells as 804G cells, that can modulate the organization of hemidesmosomal antigens in unrelated cells maintained upon it. This effect appears specific to hemidesmosomal elements since adhesion plaque components do not obviously change their localization in cells maintained upon the matrix of the present invention.

To demonstrate this new discovery, evidence is provided that the rat 804G matrix was capable of inducing assembly of "mature" hemidesmosomes in human epidermal carcinoma (SCC12) cells. It can be appreciated that it is uncommon to find compounds from rodent cells that have such a profound effect on human tissue. In these experiments, described in more detail below, an increased number of hemidesmosome-like structures were found in SCC12 cells maintained upon the 804G matrix as compared to control experiments wherein SCC12 cells were grown on rat tail collagen. Moreover, the majority of these hemidesmosome-like structures in the 804G matrix grown cells were in contact with the cell substrate and possessed basal dense plates. The latter structures are often used as indicators of mature or formed hemidesmosomes (Krawczyk and Wilgram, 1973).

Although methods related to production and isolation of the 804G cell matrix are specifically disclosed, it can be appreciated that any cell matrix having the ability to support cell adhesion and hemidesmosome assembly is within the scope of the present invention. Matrices from other cell types, such as the rat bladder carcinoma cell line NBT II (ATCC CRL 1655) also appear to be able to induce attachment and hemidesmosome assembly in vitro. It should be noted that the term "804G Matrix" is used to generically refer to any cell matrix with the ability to stimulate cell attachment and hemidesmosome formation. As defined herein, 804G matrix is comprised of one or more protein components secreted by 804G rat bladder carcinoma cells which facilitate hemidesmosome formation in epidermal cells and keratinocytes.

One major use contemplated for the active components of the matrix of the present invention is in cell growth and attachment. A substrate upon which cells are to be grown is coated with the matrix or with purified hemidesmosome-promoting components thereof. The cells to be grown are then plated or applied to the substrate, and grown on the matrix. Such cells, including human cells in vitro and in vivo, will grow in an organized fashion on the substrate and will form hemidesmosomes. Hemidesmosome formation is a major advantage, because it greatly enhances the attachment of the cells to the substrate. Furthermore, it appears that the organization of cells growing on the matrix is significantly more advanced, more tissue-like, than cells grown without the matrix of the present invention.

The substrate used herein may be any desired substrate. For laboratory use, the substrate may be as simple as glass or plastic. Alternatively, any suitable substrate may be used, including various shaped articles, fabrics, prosthetic implants, and the like. For use in vivo, the substrate may be any biologically compatible material on which cells can grow. Suitable substrate materials may include shaped articles made of or coated with such materials as collagen; regenerated collagen; polylactic acid; biocompatible metals such as stainless steel and titanium; ceramic materials including prosthetic materials such as hydroxylapatite; synthetic polymers, including polyesters and nylons; biological materials that are actually part of a patient, such as bones and teeth, and virtually any other material to which biological molecules can readily adhere.

A specific use of the present invention is for generating skin for allograft use. Epidermal cells, for example, are seeded onto a substrate of the present invention. These cells are grown on the substrate using conventional skin growth conditions, including nutrients and growth factors. The improvement of the present invention, that is, the use of the hemidesmosome-promoting matrix on the substrate, improves such ex vivo growth of skin over prior art techniques that do not use that matrix.

One particular use of the present invention is to increase epidermal cell adhesion to target surfaces. For instance, prostheses for dental implantation may be treated with the 804G matrix to stimulate periodontal cell attachment. Existing teeth may similarly be coated with the matrix as a treatment for gum (junctional epithelium) disease, such as gingivitis. Where a substrate is made of a natural or synthetic bioerodible material in the form of a sheet or fabric, such as woven or bonded collagen or polylactic acid, the matrix materials may be applied to the surface thereof or mixed in with the composition. Cells (such as epidermal cells) may then be grown on the matrix ex vivo to form transplantable or implantable materials; alternatively, the materials may be implanted and cells may be permitted to attach in vivo.

Another preferred embodiment of the present invention is the growth of increased numbers of endocrine precursor cells. Particularly interesting are pancreatic islet cell precursors. For example, fetal pancreatic islet-like cell clusters may be grown in vitro in the presence of 804G matrix-type proteins for transplantation into diabetic patients. The 804G matrix will increase the yield of fetal ICCs for transplantation and will thus solve the established need for greater numbers of these cells. Since the matrix of the NBTII rat bladder carcinoma cell line is also able to promote increased epidermal cell growth, its use as a matrix for the growth of fetal pancreatic ICCs is advantageously envisioned, as is any such "804G" matrix protein, including all such proteins secreted by cell lines which are capable of promoting hemidesmosome formation in epidermal cells. In addition, the inclusion of growth factor in the ICC culture medium will further increase the yield of fetal pancreatic ICCs.

The resulting cell clusters will differentiate into functional pancreatic endocrine cells after transplantation into mammals, preferably humans, and will reduce or eliminate the need for insulin injections. Interestingly, 804G matrix has cross-species activity; even matrix derived from rat bladder carcinomas has the ability to promote growth and hemidesmosome formation in human tissue.

The 804G matrix will also be of great use in studies concerning hemidesmosome morphogenesis, $\alpha_6\beta_4$ integrin interactions with the extracellular matrix and for functional and structural analyses of new matrix components such as the laminin B2t-like rat molecule described below. Indeed, the 804G matrix may prove to be a tool that allows definition of hemidesmosome-mediated interactions between epithelial cells and the underlying connective tissues at the molecular level.

The 804G matrix of the present invention comprises four concanavalin-binding glycosylated proteins, of approximately 135 kD, 140 kD, 150 kD, and 400 kD, and a non-glycosylated, non-concanavalin binding protein of about 85 kD, all of which are recognized by polyclonal antibody raised against the 804G matrix. The methods of the present invention may be practiced with the complete, active matrix from 804G cells or a functionally equivalent "804G" matrix from other cells, and may also be practiced with any one of the individual protein components of the matrix which promotes hemidesmosome formation. Cell matrix and matrix proteins can be readily screened for the ability to facilitate hemidesmosome formation, using the techniques described herein. Only routine empirical testing is required.

In addition to the active matrix and the active components thereof, the present invention also includes shaped articles coated with those materials. Preferably, those shaped articles are formed of materials other than glass, and include such forms as sheets, fabrics, prostheses, metal articles, bioerodible articles, and implantable articles.

Furthermore, pharmaceutical preparations of the active matrix or its active components are contemplated. These preparations can be in any suitable form, and generally comprise the active ingredient in combination with any of the well known pharmaceutically acceptable carriers. The matrix material may be harvested (as by scraping, abrading, or treatment with low concentrations of SDS) from surfaces on which appropriate matrix-depositing cells have been grown. Alternatively, the matrix materials may be prepared synthetically or through recombinant DNA techniques, or through purification of deposited matrix material. Those carriers can include injectable carriers, topical carriers, transdermal carriers, and the like. The preparation may advantageously be in a form for topical administration, such as an ointment, gel, cream, spray, dispersion, suspension, or paste. The preparations may further advantageously include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton Pa. (1975), the relevant disclosure of which is hereby incorporated by reference.

Finally, epithelial cells of various types may be grown on the substrates or with the compositions contemplated herein.

EXAMPLE 1

Preparation of 804G Cell Matrix

To begin biochemical characterization of the matrix secreted by the 804G cells, we followed the procedure of Gospodarowicz (1984). Briefly, rat bladder carcinoma 804G cells were maintained at 37° C. in MEM with Earle's salts supplemented with 50 U/ml penicillin, 50 µg/ml streptomycin and 10% FCS (GIBCO LABORATORIES, Grand Island, N.Y.). This medium contains approximately 1.9 mM $Ca^{2+}$.

The 804G cells were grown to confluency on either plastic Petri dishes or glass coverslips. The culture medium was then discarded and the cells washed in sterile PBS. The cells were removed from their matrix by treatment for 5 minutes in sterile 20 mM $NH_4OH$, followed by three rapid washes with sterile distilled water.

The matrix was removed from the substrate by solubilization in 8M urea, 1% sodium dodecyl sulfate (SDS) in 10 mM Tris, pH 6.8. The 804G matrix polypeptide profile was analyzed by Sodium Dodecylsulfate Polyacrylamide Gel Electrophoresis (SDS-PAGE) using routine experimental methods known to those with skill in the art.

A preparation having approximately 20 µg of the solubilized 804G cell matrix was loaded onto an acrylamide gel and electrophoresed. As a control, an extract from the intact 804G cells, having approximately 20µg per lane, was also loaded onto the acrylamide gel. Following gel electrophoreses we noted that there were three major polypeptides in the matrix preparation ranging in molecular weight from 150–135 kD. A minor polypeptide of 85 kD was also present in the matrix preparation. After PAGE, the separated polypeptides were transferred to nitrocellulose by standard well known methods. Amido black stains of the dyed protein samples were transferred to the nitrocellulose indicating a successful completion of the Western Blotting procedure.

EXAMPLE 2

Concanavalin Binding to 804G Matrix

A strip of the Western Blot nitrocellulose containing separated matrix proteins was incubated with Concanavalin A. Non-specific protein binding to the matrix molecules was blocked by first incubating the strip for 30 minutes at room temperature with 2% (w/v) polyvinylpyrrolidone in PBS. Concanavalin A was added to the blocking buffer and the filter was then incubated with gentle shaking at room temperature. Horse radish peroxidase (HRP) was added to visualize Concanavalin A binding.

Four matrix polypeptides of 135, 140, 150 and 400 kD were recognized by Concanavalin A. As is known in the art Concanavalin A binding indicates that these matrix components are glycosylated. To identify proteins on the Western Blot that were specific to the matrix, we raised polyclonal and monoclonal antibodies.

EXAMPLE 3

Production of Polyclonal Antibodies Against the 804G Matrix

Antiserum was prepared by injecting urea/SDS solubilized 804G cell matrix, as described above, into a rabbit by standard methods. Briefly, solubilized 804G matrix was mixed with Freund's adjuvant and injected into a rabbit. Serum was collected at three weekly intervals following one booster injection as detailed by Harlow and Lane (1988).

The isolated polyclonal antiserum (J18) had antibodies recognizing the four 135–400 kD species that bound concanavalin A, as well as an 85 kD polypeptide. Therefore, there appears to be a non-glycosylated 85 kD species in the matrix along with four additional glycosylated polypeptides.

Following our experiments with the polyclonal antibodies, we produced monoclonal antibodies specific for the 804G matrix by the following method.

EXAMPLE 4

Production of Monoclonal Antibodies Against the 804G Matrix

A mouse monoclonal IgG (5C5) against the 804G cell matrix was prepared by injecting a solubilized 804G cell matrix sample into several mice. At two and three weeks after the initial injection the mice were boosted with further 804G matrix injections. Five days following the final boost their spleens were removed and isolated spleen cells were fused with the myeloma cell line Sp2 for the production of hybridomas using standard techniques (Galfre and Milstein, 1981). Hybridoma cells producing antibody against matrix elements were selected on the basis of their immunoblotting and immunofluorescence reactivities against matrix samples. Selected hybridoma cells were cloned twice by limited cell dilution as described in Harlow and Lane, 1988.

Western Blots with one of the mouse monoclonal IgG antibodies (5C5) recognized only a 150 kD and a 135 kD polypeptide in the matrix preparation. Antibody 5C5 and the J18 serum were then used in immunoprecipitation studies to investigate potential protein-protein interactions in the matrix.

EXAMPLE 5

Immunoprecipitation Studies of the Matrix

Immunoprecipitation of the 804G matrix was performed using conventional methodology. In brief, the 804G matrix was treated with RIPA buffer (0.1M Tris-HCl, pH 7.2, containing 0.15M NaCl, % Triton X100, 0.1% SDS, 1% Na deoxycholate, 10 mM EDTA, 1 mM phenylmethylsulfonyl fluoride), clarified by centrifugation, and incubated with either the rabbit serum J18 or monoclonal antibody 5C5. The resulting antibody-antigen complexes were immunoprecipitated with *Staphylococcus aureus* Protein A by methods known to those with skill in the art.

The immunoprecipitated molecules were separated by SDS-PAGE and transferred to a Western blot by the methods described in more detail above. Lanes 1 and 2 from the gel were immunoblotted with either goat anti-rabbit, or goat anti-mouse antibodies, conjugated to HRP for visualization.

The polyclonal J18 antibodies recognized similar sets of polypeptides in both the matrix and 5C5 immunoprecipitate. Major protein bands were found in both samples at 150, 140 and 135 kD. This result indicated that the J18 serum contained antibodies against all of the major proteins of the matrix.

5C5 antibodies recognized primarily 150 kD and 135 kD polypeptides in both the 804G matrix and J18 immunoprecipitate. In contrast, the 5C5 antibodies apparently precipitated all of the molecular species in the matrix that are recognized by the J18 serum antibodies. As the 5C5 antibodies were able to precipitate most of the matrix proteins, yet only identified two proteins on a denaturing gel, we believe that the major proteins interact and are associated with one another in their normal state.

To investigate the protein composition of the 804G matrix, we probed a Western Blot of solubilized matrix proteins with polyclonal serum against the 400 kD and 200 kD chains of Engelbreth-Holm-Swarm (EHS) laminin.

Example 6

Western Blot of Matrix Proteins Probed with Anti-laminin Antibodies

Polyclonal antibodies against the 400 kD and 200 kD chains of EHS laminin were purchased from Collaborative Research Incorporated (Bedford, Mass.). A preparation of laminin (approximately 10μg per lane) and a preparation of the solubilized 804G cell matrix (approximately 20μg per lane) were denatured and run on a SDS gel, then subsequently transferred to nitrocellulose. We noted that the amido black stain used on the proteins run in lanes 1 and 2 was transferred to the nitrocellulose filter indicating that the blotting was successful.

Incubation with the HRP conjugated anti-laminin polyclonal antibodies resulted in a strong reactivity in the laminin lanes, but there was very little detectable reactivity between the laminin polyclonal antibodies and the 804G cell matrix preparation. In a related experiment, the Western Blot was immunoblotted with labeled samples of either rabbit polyclonal anti-804G serum J18 or the monoclonal antibody 5C5, respectively. These antibodies failed to recognize any laminin polypeptides, although they did recognize polypeptides in the matrix preparation as expected from previous experiments described above.

It appeared that there was little antibody cross-reactivity between laminin and the 804G matrix. For this reason, we attempted to isolate genes expressing polypeptides reactive with the J18 anti-804G antibodies.

EXAMPLE 7

Isolation of Clones Corresponding to Matrix Polypeptides

A human keratinocyte lambda gt11 expression library was purchased from Clontech Labs., Inc., Palo Alto, Calif. and screened with the 804G matrix polyclonal serum J18 according to Huynh, et al., (1985). Antibodies absorbed by the fusion protein products of these three clones showed reactivity with both 140 kD and 85 kD molecular weight species in an 804G matrix preparation and a whole cell extract of SCC12 cells (Langhofer et al., (1993) *J. Cell Sci.*, 105: 753–764).

To further characterize positive clones, plaque lifts of nitrocellulose-bound fusion proteins were used to epitope select antibodies (Sambrook, et al., 1989). cDNA inserts were subcloned into M13 vectors and sequenced by the Sanger dideoxychain termination method (Sanger, et al., 1977). Sequence analyses were made using the GCG sequence analysis software package (University of Wisconsin Biotechnology Center, Madison, Wis.).

The nucleotide sequence of these clones revealed that they encode a region spanning amino acids 550–810 in domain I/II of a recently identified variant of the B2 chain of laminin that has been termed laminin B2t (Kallunki, et al., 1992). The B2t variant is not contained in EHS laminin, and therefore represents a new subunit. This experiment illustrates the cross-reactivity of the matrix associated polypeptides with the laminin B2t variant. In addition, an 804G expression library (Invitrogen, San Diego, Calif.) was screened with both the J18 and 5C5 monoclonal antibody and clones were characterized by epitope selection. Clones containing the 150, 140 and 135 kDa proteins of the matrix were isolated. Analysis of cDNAs encoding the 140 kDa protein revealed that their nucleotide sequences exhibited significant identity with regions of the human laminin B2t gene. The small stretches of sequence for the 150 and 135 kDa components have been obtained which do not exhibit similarity with any sequences in the database.

Following this experiment we attempted to ascertain the location of 804G matrix polypeptides in intact tissue samples.

EXAMPLE 8

Immunofluorescence Localization of 804G Matrix Antigens in Intact Tissue 804G cells were processed for immunofluorescence using the 5C5 monoclonal and J18 polyclonal antibodies. Initially, the 804G cells were fixed and extracted for 2–3 min in 20° C. acetone prior to antibody incubation. Double labeling was carried out as detailed below.

Cells on coverslips were first incubated in a mixture of primary antibodies for 1 hr at 37° C. The coverslips were extensively washed in PBS and then overlaid with the appropriate mixture of rhodamine and fluorescein conjugated secondary antibodies by well known methods. Processed tissues were viewed on a Zeiss Photomicroscope III fitted with epifluorescence optics while cultured cells were viewed on a Zeiss laser scan microscope (LSM10) equipped with Argon and HeNe lasers for dual fluorescence confocal imaging (Carl Zeiss, Thornwood, N.Y.). As controls for the immunofluorescence analysis, cells were incubated in normal mouse, rat or rabbit IgG as well as secondary antibodies alone in order to assess staining due to non-specific antibody binding. Both J18 and 5C5 antibodies produced substrate staining in the 804G cell cultures. This staining is in a pattern and localizes with hemidesmosomal plaque staining in each 804G cell.

Both the J18 serum, 5C5 antibodies and the antibodies selected from the J18 serum using the laminin B2t fusion proteins were localized in cryo-sections of rat epithelial tissues by immunofluorescence microscopy. All of these antibody preparations show intense staining along the region of epithelial-connective tissue interaction.

All of the above experiments have been related to the structure and function of the 804G matrix. Thus far, we have determined that the 804G matrix peptides immunologically related to the B2t laminin variant, and that antibodies directed against matrix proteins have been found at t2he epithelial-connective tissue juncture.

One important aspect of the present invention is our discovery that the 804G matrix, described in detail above, can unexpectedly provide a substrate capable of stimulating epithelial cell growth in vitro. We discovered that epithelial cells grown on the 804G matrix produced hemidesmosomes, as expected from normal cells exhibiting an in vivo morphology. To illustrate this aspect of the invention, we performed the following experiments. Initially, we grew the SCC12 human tumor cell line on the 804G matrix to determine its potential for normal growth in vitro.

EXAMPLE 9

Functional Analyses of Epithelial Cells Grown on the 804G Matrix

Antibodies against a 230 kD plaque component of the hemidesmosome have been detailed before (Klatte et al., 1989). Monoclonal and polyclonal antibodies directed against the cytoplasmic domain (N-terminus) of a 180 kD type II membrane element of the hemidesmosome have been described in Hopkinson et al., (1992) and Riddelle et al. (1992). An antibody against the $\beta_4$ integrin subunit was purchased from Telios (San Diego, Calif.).

SCC12 cells were maintained on the 804G cell matrix for 24 hrs to assess the impact of the matrix on hemidesmosome protein localization in a tumor cell line that, under normal circumstances, does not assemble bona fide hemidesmosomes in vitro. We chose to complete our studies in 24 hrs to minimize matrix degradation and/or modification by the added cells, a possibility that Carter, et al. (1990) have discussed. Each experiment was repeated at least four times involving the analysis of more than 500 cells. As controls, the SCC12 were plated onto other matrices, such as glass and rat tail collagen. After 24 hrs the cells were processed for indirect immunofluorescence using antibodies directed against the 230 kD, 180 kD and $\alpha_6\beta_4$ integrin components of the hemidesmosome, double labelled with antibodies against the 804G cell matrix.

Cells on coverslips were first incubated in a mixture of primary antibodies for one hour at 37° C. The coverslips were extensively washed in PBS and then overlaid with the appropriate mixture of rhodamine and fluorescein conjugated secondary antibodies. Processed tissues were viewed on a Zeiss Photomicroscope III fitted with epifluorescence optics. As controls, cells were incubated with normal mouse, rat or rabbit IgG as well as secondary antibodies alone to assess staining due to non-specific background.

In SCC12 cells maintained for 24 hrs on glass and rat tail collagen, the 230 kD, 180 kD, $\alpha_6\beta_4$ integrin subunits localized to the periphery of the cells along their substratum attached surfaces. The staining sometimes resembled a fuzzy band surrounding the cell periphery, or linear streaks near the cell edges (see also Hopkinson, et al., 1991). Anti-matrix antibodies in the J18 serum generated a diffuse staining along the region of cell-substrate interaction in cells maintained on rat tail collagen, with no obvious correlation to the staining generated by the hemidesmosomal antibody probes. The reactivity of J18 antibodies with the SCC12 cells by immunofluorescence is consistent with the positive immunoblotting reactivity using antibodies selected from the J18 serum by the human laminin B2t fusion proteins. Since antibodies in the J18 serum failed to recognize rat tail collagen alone, our results provide some indication concerning the matrix that the SCC12 cells themselves secrete.

In SCC12 cells maintained on the 804G cell matrix, the 230 kD, 180 kD and $\alpha_6\beta_4$ integrins show a dramatically different pattern of distribution compared with that observed in cells maintained on rat tail collagen or glass. The patterns that these hemidesmosomal antibodies generate are similar to that seen in 804G cells processed for immunofluorescence using the same antibodies, as described above. Furthermore, this staining, in most instances, appears coincident with those patterns generated by antibodies in the whole J18 serum.

In addition, 5C5 antibodies or those J18 antibodies epitope selected from the laminin B2t fusion proteins were also localized in SCC12 cells maintained on the 804G matrix. The distribution of these antibodies compared with that of the 230 kD hemidesmosomal plaque component. It should be noted that the 230 kD antigen distribution in the SCC12 cells mirrors that of the staining generated by the 5C5 and epitope selected antibodies.

Immunoblotting analyses were undertaken to examine whether there was a change in the amounts of both the 230 kD and 180 kD hemidesmosomal components in SCC12 cells maintained on 804G cell matrix for 24 hrs compared to SCC12 cells maintained for the same length of time on other matrices. There was no apparent difference in the quantity of both the 230 kD and 180 kD polypeptides in SCC12 cells maintained on the various matrices as assessed by this procedure.

In contrast to hemidesmosomal components, the $\alpha_5\beta_1$ integrin complex, a component of the microfilament associated-adhesion plaque (Burridge, et al. 1988), localize primarily at the peripheral cell-substratum associated surface of SCC12 cells regardless of whether it is maintained on rat tail collagen or the 804G cell matrix.

Our studies of epithelial cell growth on the 804G matrix were not confined to SCC12 cells. Normal Human Keratinocytes (derived from human foreskins), HaCaT (immortalized cells), and SCC13 cells also exhibited almost identical responses when grown on the 804G matrix in comparison to the SCC12 cells discussed above. In each of these cell types, growth on the 804G matrix led to a redistribution of integrins and mature hemidesmosome formation.

In addition, experiments similar to those described above have been performed on the matrix produced by the NBTII cell line. The results from these experiments are virtually identical to those illustrated for the 804G matrix. Cells grown on the NBTII matrix were stimulated to form mature hemidesmosomes and redistribute cell surface integrins.

To further investigate the effect of growing epithelial cells on the 804G matrix, we examined SCC12 cells under the electron microscope.

EXAMPLE 10

Electron Microscopic Examination of the Impact of the 804G Cell Matrix on Hemidesmosome Assembly in SCC12 Cells SCC12 cells were fixed and processed for electron microscopy as described elsewhere (Riddelle, et al., 1991). Thin sections of cells were made perpendicular to their substrate, placed on 300 mesh electron microscope grids (Tousimis Corp., Rockville, Md.), stained and then viewed at 60 kV in a JEOL 100CX electron microscope.

SCC12 cells maintained for 24 hrs on either rat tail collagen or the 804G matrix were examined by conventional electron microscopy. This procedure involved analyzing thin sections of the SCC12 cells cut perpendicularly to their substrate at intervals of 10 microns through a population of cells. By assessing sections at this distance apart we avoided the possibility of observing the same hemidesmosome more than once.

In SCC12 cells maintained for 24 hrs on rat tail collagen, hemidesmosome-like structures were observed towards the cell periphery. In 17 SCC12 cells incubated on rat tail collagen we observed 9 hemidesmosome-like structures, none of which possessed a basal dense plate. This count was made over a distance of 306 microns (i.e. 1 hemidesmosome-like structure/34 microns of the ventral surfaces of SCC12 cells). The close apposition of three hemidesmosome-like structures was seen in one micrograph, however, this was highly unusual. In many basal profiles of SCC12 cells on rat tail collagen no hemidesmosomes were observed.

In contrast, 103 hemidesmosome-like structures, of which 92 possessed basal dense plates, were observed in cross sectional profiles of SCC12 cells incubated on the 804G matrix. These observations were made over a distance of 504 microns (i.e., 1 hemidesmosome-like structure/4.9 microns of SCC12 ventral surface). Unlike the "rudimentary" hemidesmosomes seen on cells incubated with rat tail collagen, these hemidesmosome-like structures were not confined to the periphery of the cell, but also were found underlying the nucleus. These SCC12 cells also appeared to possess tufts of intermediate filaments associated with their cytoplasmic face.

In addition to electron microscopy of SCC12 cells, we looked for hemidesmosome assembly in Human Keratinocytes, HaCaT cells, and SCC13 cells. As reported above in relation to immunofluorescence experiments, each of these other mammalian epithelial cells began redistributing integrins and forming mature hemidesmosomes. Our electron microscope studies revealed significant similarities in the effect of the 804G matrix on SCC12 cells, Human keratinocytes, HaCaT cells, and SCC13 cells.

To demonstrate that the 804G cell matrix could retain its ability to induce changes in epithelial cells after solubilization, we coated glass coverslips with solubilized matrix elements.

EXAMPLE 11

Photolithography with 804G Matrix Elements

To determine whether an isolated matrix sample could retain its ability to induce changes in hemidesmosomal and integrin localization 804G cells were grown and removed from their matrix as described above. A mild SDS buffer (RIPA) was used to solubilize and remove the matrix from its growth substrate. Following solubilization in RIPA buffer, the matrix elements were dialyzed extensively against phosphate buffered saline and then coated in a microscopic pattern onto glass coverslips using a photolithographic technique described by Hockberger et al. (*Journal of Neuroscience* (1988) 8 (11): 4098–4120).

Briefly, a clean coverslip was first spin-coated with "photoresist". A mask was placed on top of the photoresist layer followed by illumination with UV light. At all of the points not covered by the mask the photoresist was UV cross-linked to the glass coverslip. Dialyzed 804G matrix elements were then added to the coverslip and bound along the entire surface of the coverslip. The photoresist and its bound matrix elements were removed from the non-UV linked areas of the coverslip by acetone treatment. A defined pattern of 804G matrix elements, configured as the inverse of the mask, was retained for further examination.

In immunofluorescence studies using our matrix polyclonal antiserum, we demonstrated that SCC12 cells grown on these coverslips form hemidesmosomes in formations corresponding to the deposited pattern of 804G elements. Remarkably, the location of $\beta_4$ integrins on SCC12 cells grown on these coverslips also followed the deposited matrix patterns. This indicated that the matrix maintained its functionality following mild SDS denaturation and deposit onto a solid substrate. By following this protocol, other solid substrates could be coated with the 804G matrix to stimulate hemidesmosomal formation in epithelial cells.

Thus, we have demonstrated that the 804G cell matrix is able to induce attachment and hemidesmosome assembly in many types of mammalian cells.

EXAMPLE 12

Expansion of fetal pancreas islet cells in vitro

Human fetal pancreases are minced into 1 mm pieces in cold Hanks' balanced salt solution (HBSS) and digested with collagenase P by shaking vigorously for 15 min in a water bath at 37° C. After several washes at 4° C. with HBSS, the digested tissue is washed with cold HBSS and placed into petri dishes in RPMI-1640 medium containing 10% pooled human serum and antibiotics for three days. Optionally, a growth factor is present during this procedure.

Approximately 50 ICCs of uniform size (50–75 µM diameter) and homogeneous translucent appearance are hand picked and plated on tissue culture dishes coated with either 804G matrix or bovine corneal matrix in RPMI-1640 containing 15% horse serum, 5% FCS, antibiotics and, optionally, a growth factor. ICCs attach overnight and monolayer formation is generally initiated by 24 hours. A significant increase is observed in the number of ICCs plated on 804G matrix compared to either no matrix or to bovine corneal matrix.

To determine whether these fetal endocrine cells are capable of differentiating into insulin-producing cells in vivo, ICCs are transplanted as described below.

EXAMPLE 13

Transplantation of ICCs into nude mice

ICCs from Example 12, cultured on 804G matrix, are transplanted under the kidney capsule of athymic nude mice (approximately 500 ICCs per mouse) and the grafts are analyzed after 3 months. An increased level of human C-peptide, released into the blood after processing of the insulin precursor molecule, is detected in the blood of grafted animals by radioimmunoassay after an intraperitoneal glucose challenge indicating that the grafted cells are able to produce insulin. In addition, immunocytochemistry of graft cells using an antibody to insulin indicates that the precursor cells differentiate into insulin-producing cells.

Transplantation of ICCs into diabetic patients

Human diabetes patients are administered a number of fetal ICCs to be optimized in clinical studies. Presumably, this number will be close to that used for adult-derived cells, approximately $2-8 \times 10^5$, either by implantation under the kidney capsule or by direct injection into the liver. In addition, transplantation in other ectopic organ locations is also contemplated. C-peptide production and blood glucose levels are monitored over several months to determine whether transplanted endocrine precursor cells have differentiated into insulin-producing cells. The patients are still administered insulin during the monitoring period.

It should be noted that the present invention is not limited to only those embodiments described in the Detailed Description. Any embodiment which retains the spirit of the present invention should be considered to be within its scope. However, the invention is only limited by the scope of the following claims.

What claimed is:

1. A method for growing cells of pancreatic islet-like cell clusters (ICCs), comprising the step of culturing said ICCs in contact with a laminin-like extracellular matrix material that is produced by 804G cells and NBT-II cells, wherein said matrix material comprises three polypeptides having molecular weights of about 150 kD, 140 kD and 135 kD, said matrix material characterized as:

(a) promoting enhanced growth of said ICCs in comparison to ICCs grown without the extracellular matrix material;
   (b) having the ability to promote hemidesmosome formation in epithelial cells cultured thereon;
   (c) binding concanavalin; and
   (d) being bound by polyclonal antibodies generated against the extracellular matrix secreted by 804G or NBT II cells.

2. The method of claim 1, further comprising performing the following steps prior to said culturing step:

enzymatically digesting fetal pancreas; and
   incubating the digested pancreas in cell culture medium until islet-like cell aggregates are formed.

3. The method of claim 2, wherein said pancreas is from a mammal.

4. The method of claim 3, wherein said pancreas is human.

5. The method of claim 1, wherein said extracellular matrix material is attached to a substrate and said ICCs are grown on said extracellular matrix material.

6. The method of claim 1, wherein said extracellular matrix material has been produced by 804G rat bladder carcinoma cells.

7. The Pancreatic ICCs prepared in accordance with claim 1.

* * * * *